(12) United States Patent
Shindome et al.

(10) Patent No.: US 10,807,044 B2
(45) Date of Patent: Oct. 20, 2020

(54) DISCHARGE MEMBER WITH FILTER

(71) Applicant: EIKEN KAGAKU KABUSHIKI KAISHA, Tokyo (JP)

(72) Inventors: Tsuyoshi Shindome, Tochigi (JP); Waka Natsume, Tochigi (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/971,612

(22) Filed: May 4, 2018

(65) Prior Publication Data

US 2018/0250636 A1 Sep. 6, 2018

Related U.S. Application Data

(63) Continuation of application No. PCT/JP2016/082519, filed on Nov. 2, 2016.

(30) Foreign Application Priority Data

Nov. 5, 2015 (JP) ................. 2015-217667

(51) Int. Cl.
*B01D 63/08* (2006.01)
*B65D 47/18* (2006.01)
(Continued)

(52) U.S. Cl.
CPC ......... *B01D 63/08* (2013.01); *B01D 39/1676* (2013.01); *B01D 69/02* (2013.01);
(Continued)

(58) Field of Classification Search
CPC .... B01D 63/08; B01D 39/1676; B01D 69/02; B01D 2325/36; B01D 2239/1208;
(Continued)

(56) References Cited

U.S. PATENT DOCUMENTS 4,678,571 A * 7/1987 Hosaka .................... C02F 1/003
   210/202
4,797,260 A * 1/1989 Parker ..................... B01D 61/18
   210/416.1
(Continued)

FOREIGN PATENT DOCUMENTS

CN 1972755 A 5/2007
CN 102725073 A 10/2012
(Continued)

OTHER PUBLICATIONS

International Search Report issued in International Application No. PCT/JP2016/082519, dated Jan. 24, 2017 (2 pages).
(Continued)

*Primary Examiner* — Lien M Ngo
(74) *Attorney, Agent, or Firm* — Osha Liang LLP

(57) ABSTRACT

A discharge member with a filter enables a filtrate to be dripped into a dripping container while filtering a suspension, and enables an excessive portion to be suctioned when the dripped amount is excessive, thereby to allow a fixed amount of a filtrate to be injected into the dripping container. The discharge member may enable suctioning operation at the time of suctioning an excessive portion to be conducted without deteriorating its dripping performance and filtering performance. The filter provided in the discharge member is a composite filter in which a pre-filter including a continuous porous foam that is softened at least in a wet state is arranged on a filtration surface side of a membrane filter.

4 Claims, 5 Drawing Sheets

(51) Int. Cl.
*G01N 1/10* (2006.01)
*B01D 39/16* (2006.01)
*B01D 69/02* (2006.01)
*B05B 11/04* (2006.01)
*G01N 1/14* (2006.01)
*G01N 1/40* (2006.01)
*C12M 1/00* (2006.01)

(52) U.S. Cl.
CPC ............ *B05B 11/047* (2013.01); *B65D 47/18* (2013.01); *G01N 1/10* (2013.01); *G01N 1/14* (2013.01); *G01N 1/4077* (2013.01); *B01D 2239/0421* (2013.01); *B01D 2239/065* (2013.01); *B01D 2239/1208* (2013.01); *B01D 2239/1216* (2013.01); *B01D 2325/36* (2013.01); *C12M 1/00* (2013.01); *G01N 2001/4088* (2013.01)

(58) Field of Classification Search
CPC ............ B01D 2239/1216; B05B 11/04; B05B 11/047; B65D 47/18; G01N 1/10; G01N 1/14; G01N 1/4077; G01N 2001/4088; C12M 1/00
USPC ......... 222/189, 189.06, 189.09, 189.11, 420; 422/549, 550, 512, 547, 554, 556, 534, 422/535; 604/295
See application file for complete search history.

(56) References Cited

U.S. PATENT DOCUMENTS

| | | | | |
|---|---|---|---|---|
| 5,514,341 | A * | 5/1996 | Urata | A61B 10/0038 422/534 |
| 6,959,615 | B2 * | 11/2005 | Gamble | G01N 1/38 422/547 |
| 7,744,820 | B2 * | 6/2010 | Togawa | B01D 61/18 210/348 |
| 8,192,699 | B2 * | 6/2012 | Ziegmann | B01L 3/0275 422/524 |
| 8,263,390 | B2 * | 9/2012 | Tajima | B01L 3/0275 422/405 |
| 8,771,615 | B2 * | 7/2014 | Shibata | B65D 47/06 422/550 |
| 8,999,167 | B2 * | 4/2015 | Nakano | A61M 1/3633 210/490 |
| 9,402,765 | B2 * | 8/2016 | Chibret | A61F 9/0008 |
| 2002/0000403 | A1 * | 1/2002 | Tanaka | A61M 1/3633 210/263 |
| 2007/0090044 | A1 * | 4/2007 | Mihashi | A61F 9/0008 210/473 |
| 2008/0067194 | A1 | 3/2008 | Faurie | |
| 2008/0261807 | A1 * | 10/2008 | Chevigny | A61L 15/18 502/402 |
| 2009/0152302 | A1 * | 6/2009 | Grevin | B65D 47/18 222/189.06 |
| 2010/0044337 | A1 | 2/2010 | Shibata et al. | |
| 2010/0251955 | A1 * | 10/2010 | Knoll | G02F 1/1525 116/206 |
| 2011/0052459 | A1 | 3/2011 | Shibata et al. | |
| 2011/0297610 | A1 * | 12/2011 | Auras | B01J 20/226 210/435 |
| 2012/0006225 | A1 * | 1/2012 | Tsukiana | C09D 11/322 106/31.86 |
| 2012/0305599 | A1 | 12/2012 | Painchaud et al. | |
| 2013/0028814 | A1 * | 1/2013 | Numai | C12N 15/1017 422/534 |
| 2014/0158604 | A1 * | 6/2014 | Chammas | B32B 1/02 210/256 |
| 2014/0276330 | A1 * | 9/2014 | Costa | A61F 5/0076 604/8 |

FOREIGN PATENT DOCUMENTS

| | | |
|---|---|---|
| JP | H09-68484 A | 3/1997 |
| JP | 5432891 B2 | 3/2014 |
| WO | 2008/090806 A1 | 7/2008 |
| WO | 2009/130948 A1 | 10/2009 |

OTHER PUBLICATIONS

International Preliminary Report on Patentability issued in International Application No. PCT/JP2016/082519, dated May 17, 2018 (8 pages).
H. Ushikubo. "The principal of LAMP method—A simple and rapid gene amplification method-". The Japanese Society or Virology, Virus, 2004, vol. 54, Issue 1, pp. 107-112 with English Translation of Abstract (6 pages).
Public Interest Incorporated Association, Japan Anti-Tuberculosis Association, Double-Crosspiece Cross, Jul. 2011, No. 339, pp. 11-13 (3 pages).
Extended European Search Report issued in European Application No. 16862103.5, dated Apr. 10, 2019 (6 pages).
Office Action issued in Chinese Application No. 201680061901.9, dated Mar. 21, 2019 (12 pages).

* cited by examiner

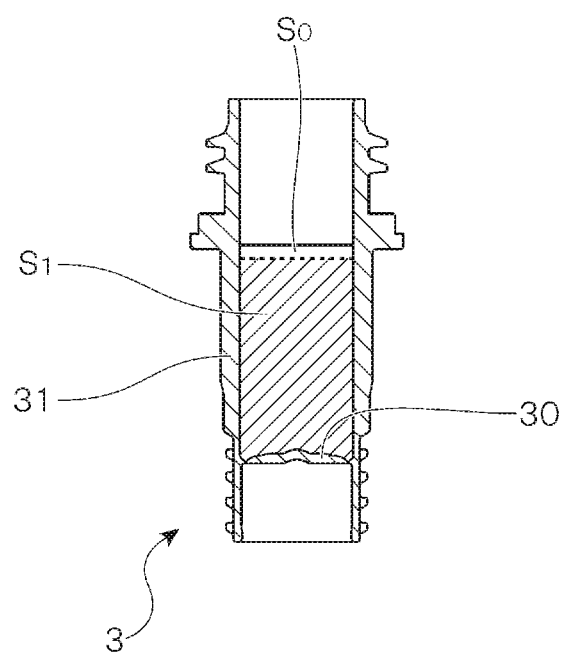
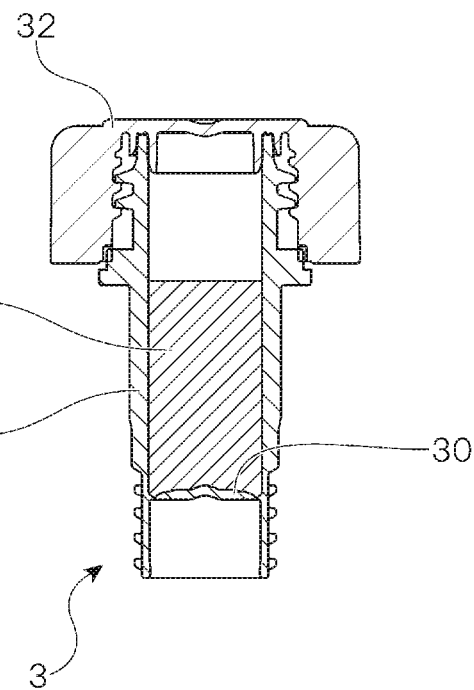
FIG.2A
FIG.2B

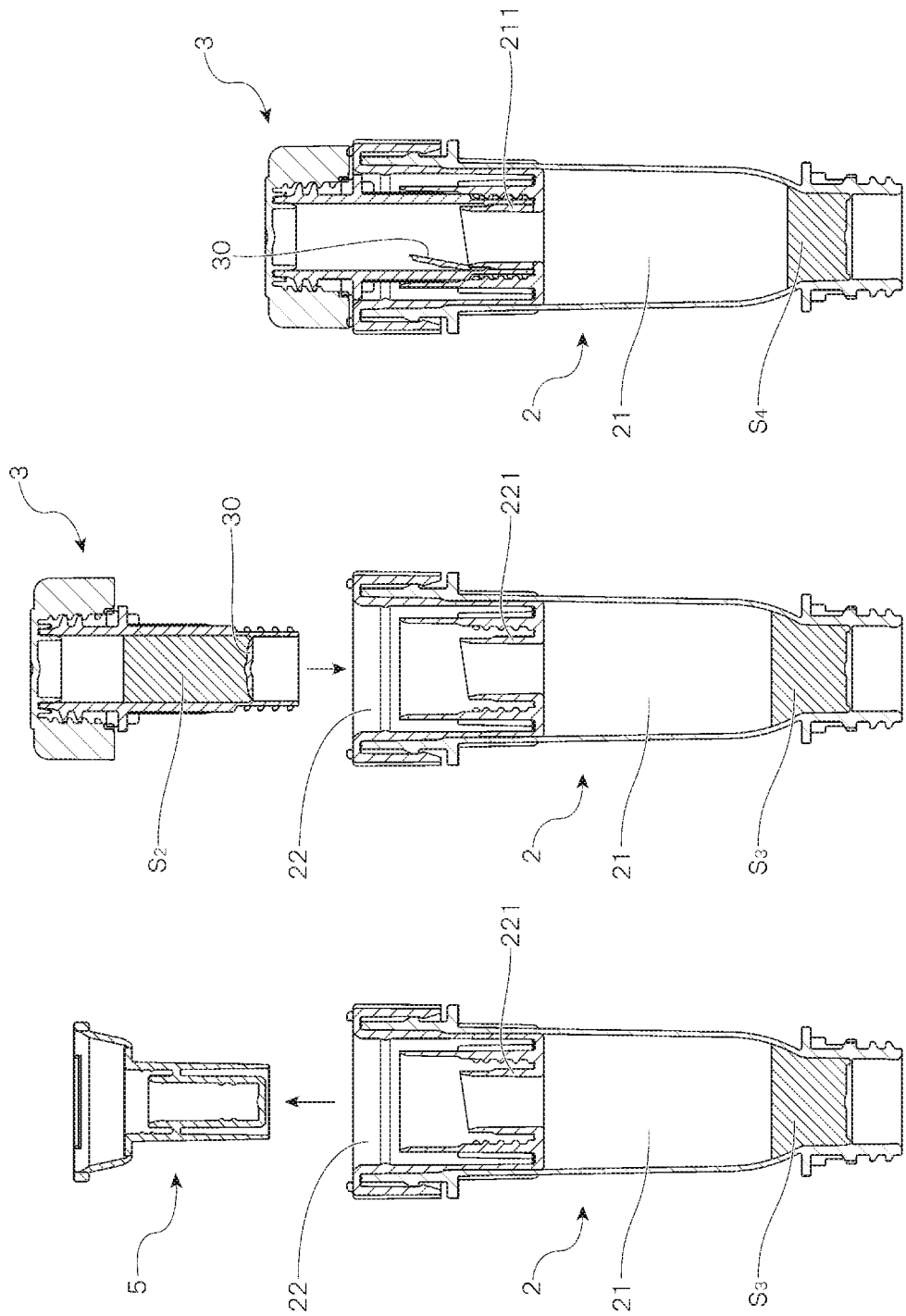

DISCHARGE MEMBER WITH FILTER

TECHNICAL FIELD

One or more embodiments of the present invention relate to a discharge member with a filter for dripping a fixed amount of a filtrate while filtering a suspension.

BACKGROUND

A genetic testing is conducted in various fields including diagnosis of infectious diseases.

In a genetic testing, in order to detect a slight amount of a target gene contained in a specimen, it is required to amplify such gene. Conventional gene amplification methods may include a large number of steps and complicated procedures, leading to an increase in cost, etc. Therefore, the applicant developed a gene amplification method (LAMP method) that is capable of amplifying efficiently only a target gene and also is capable of easily detecting the amplified target gene by incubating a sample containing a target gene to be amplified together with a prescribed reagent at a prescribed temperature (see Non-Patent Document 1).

The applicant has proposed a composite container that is preferably used in such gene amplification method, in which, in order to enable a simple and safe genetic testing, a process of heating a specimen in a treatment liquid to inactivate bacterium to allow a nucleic acid to be eluted from the bacterial cell and a process of removing impurities are conducted in a single container, whereby a specimen preparation liquid (DNA extraction liquid) can be prepared while keeping the state isolated from the external environment (see Patent Document 1). Such a composite container is widely used as a tuberculosis diagnosis kit, for example (see Non-Patent Document 2).

RELATED ART DOCUMENTS

Non-Patent Documents

Non-Patent Document 1: The Japanese Society for Virology, Virus, Vol. 54, issue 1, pp. 107-112, 2004

Non-Patent Document 2: Public Interest Incorporated Association, Japan Anti-Tuberculosis Association, Double-Crosspiece Cross, No. 339, pp. 11-13, 7/2011

Patent Document

Patent Document 1: Japan Patent No. 5432891

Here, in the composite container of Patent Document 1, a heat-treated liquid of a specimen and an adsorbent accommodated within the container main body are stirred and mixed to remove contaminants in the heat-treated liquid of the specimen by allowing the contaminants to be adsorbed to the adsorbent, and the specimen preparation liquid is dripped from a discharge port of a discharge member into a dripping container while filtering the slurry-like suspension through a filter attached to the discharge member. The dripping container into which the specimen preparation liquid is injected is set in an amplification device, and is heated at a predetermined temperature for a predetermined period of time. Although a genetic testing is conducted by evaluating the results of the amplification reaction, in order to allow such genetic testing to be conducted accurately for a short period of time, an appropriate amount of a specimen preparation liquid is required to be injected into the dripping container.

Therefore, Patent Document 1 also proposes a method for injecting an appropriate amount of a specimen preparation liquid into a dripping container wherein an upper liquid level line that shows the upper limit of an appropriate amount of a specimen preparation liquid and a lower liquid level line that shows the lower limit of an appropriate amount of a specimen preparation liquid are marked on the dripping container, and the tip of the discharge port is positioned such that it overlaps the upper liquid level line, and if the dripped amount is significantly large, the excessive portion is suctioned from the discharge port, whereby an appropriate amount of the specimen preparation liquid is injected into the dripping container.

However, as a result of studies made by the applicant afterwards, it has been revealed that, when suctioning the specimen preparation liquid that has been dripped an excessive amount by using such method, the suctioning operation takes time, or if a malfunction is significant, the excessive portion cannot be suctioned. Under such circumstances, the applicant made further studies. As a result, the applicant found that fine particles of the adsorbent caught by the filter when filtering a suspension prevent the liquid flow at the time of the suction.

SUMMARY

That is, one or more embodiments of the present invention provide a discharge member with a filter that may be used in the above-mentioned gene amplification method, etc. which may enable suctioning operation of at the time of suctioning an excessive portion to be conducted without deteriorating its dripping performance and filtering performance in the case where a filtrate is dripped into a dripping container while filtering a suspension containing fine particles such as an adsorbent, and an excessive portion to be suctioned when the dripped amount is excessive, thereby to allow a fixed amount of a filtrate is injected into the dripping container.

The discharge member with a filter according to one or more embodiments of the present invention is as follows: a discharge member with a filter, which enables a filtrate to be dripped into a dripping container while filtering a suspension, and enables an excessive portion to be suctioned when a dripped amount is excessive, thereby to allow a fixed amount of a filtrate into the dripping container, wherein the filter that filtrates the suspension is a composite filter in which a pre-filter formed of continuous porous foam that is softened at least in a wet state is arranged on a filtering side of a membrane filter.

According to one or more embodiments of the invention, it is possible to inject a fixed amount of filtrate to a dripping container with excellent operability without the need of the skill of an operator.

BRIEF DESCRIPTION OF THE DRAWINGS

FIGS. 2A and 2B are explanatory views showing a step in which a specimen is added to a treatment liquid accommodated within a sub container, the sub container sealed with a lid body is subjected to a heat treatment together with the contents;

FIGS. 3A to 3C are explanatory views showing a step in which a sub container is attached to an attachment portion of the container main body and a heat-treatment liquid of a specimen flown into the container and the adsorbent accommodated within the container main body are stirred and mixed;

Hereinbelow, one or more embodiments of the present invention will be explained with reference to the drawings.

Figure 1:
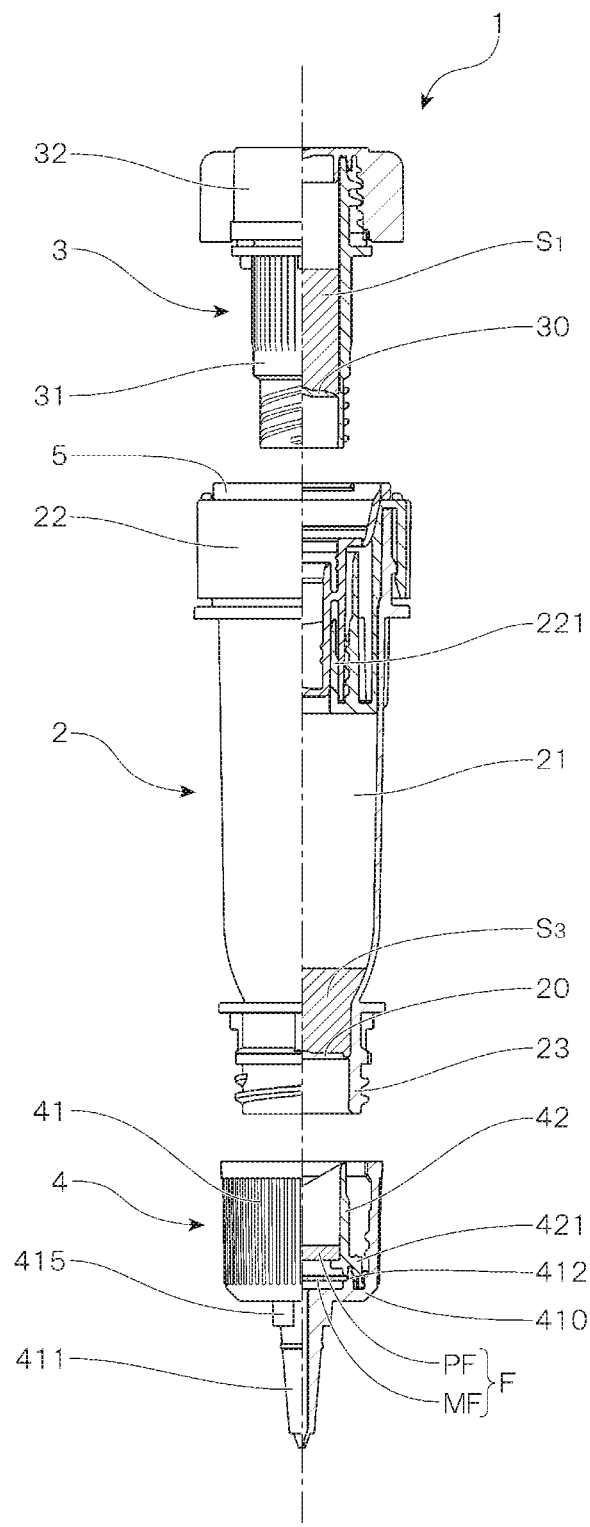
FIG. 1 is a partially-cut away cross-sectional view of essential parts showing the outline of a composite container provided with the discharge member with a filter according to the present embodiment.

FIG. 1 shows one example of a composite container 1 provided with a discharge member 4 with a filter according to the present embodiment, a container main body 2 and a sub container 3.

Such composite container 1 may be used as a container for preparing a specimen preparation liquid by treating a specimen such as phlegm collected from a subject to prepare a specimen preparation liquid when diagnosis is made whether the subject is infected with an infectious disease such as tuberculosis based on, for example, the LAMP method (see Non-Patent Document 1) developed by the applicant (see Non-Patent Document 2).

In the composite container 1 shown in FIG. 1, the sub container 3 has a cylindrical barrel portion 31 of which the upper end side is an opening portion and the lower end side is blocked by a partition wall 30 and a lid body 32 that is attached to the opening portion of the cylindrical barrel portion 31.

Further, a treatment liquid $S_1$ for heat-treating a specimen is accommodated within the sub container 3, and the inside thereof is sealed by attaching the lid body 32 to the cylindrical barrel portion 31.

The container main body 2 has a barrel portion 21 formed in a cylindrical shape, and the sub container 3 is attached to the upper end side of the barrel portion 21. At the upper end side of the barrel portion 21, an attachment portion 22 in which the sub container 3 is attached, and a cutting portion 221 that cuts a partition wall 30 of the sub container 3 at the time of attaching the sub container 3 is formed is provided. On the other hand, on the lower end side of the barrel portion 21, a contents take-out port 23 that is blocked by a partition wall 20 is provided, and the discharge member 4 with a filter is attached to this contents take-out port 23.

An adsorbent $S_3$ such as activated alumina, silica gel or zeolite is accommodated in the container main body 2, and the inside thereof is sealed by attaching a sealing member 5 to an attachment portion 22.

The discharge member 4 with a filter has an outer cylindrical portion 41 that serves as an attachment portion when it is attached to the container main body 2 and a cutting portion 42 that is attached to the inside of the outer cylindrical portion 41 and cuts the partition wall 20 of the container main body 2 when being attached to the container main body 2.

In the middle of a bottom plate portion 410 of the outer cylindrical portion 41, a discharge port 411 is formed, and at the base of the discharge port 411, a positioning protrusion portion 415 for positioning the tip of the discharge port 411 in the insertion direction when inserting the discharge port 411 into the dripping container 7 mentioned later is formed.

In this embodiment, by engagement of a cylindrical base portion 421 of the cutting portion 42 with an annular protruded portion 412 that protrudes toward the inner surface side of the bottom plate portion 410 of the outer cylindrical portion 41, the cutting portion 42 is attached to the inside of the outer cylindrical portion 41. A membrane filter MF is held between the outer cylindrical portion 41 and the cutting portion 42, a pre-filter PF 2 is held in the inside of the cylinder of the cutting portion 42. As a result, the discharge member 4 with a filter is provided with a filter F that is a composite filter by arranging the pre-filter PF on the filtration surface side of the membrane filter MF.

Details of the filter F provided in the discharge member 4 with a filter according to the present embodiment will be mentioned later.

By using such composite container 1, in order to prepare a specimen preparation liquid by treating specimens collected from a subject, first, a specimen $S_0$ is added to a treatment liquid $S_1$ accommodated within the sub container 3 (see FIG. 2A), and the sub container 3 sealed with the lid body 32 is subjected to a heat treatment together with the contents (see FIG. 2B). If bacteria such as *mycobacterium tuberculosis* is contained in the specimen $S_0$, such bacteria is inactivated by this heat treatment, and nucleic acid is eluted from the bacterial cell.

Subsequently, a sealing member 5 is removed from the container main body 2 (see FIG. 3A). The heat-treated sub container 3 is attached to the attachment portion 22 of the container main body 2 (see FIG. 3B). At this time, by a cutting portion 221 formed in the attachment portion 22, the partition wall 30 that blocks the lower end side of the sub container 3 is cut. As a result, a heat-treated liquid $S_2$ of a specimen in the sub container 3 is flown to the container main body 2 while keeping the state isolated from the external environment.

In the container main body 2, the adsorbent $S_3$ is accommodated. By shaking or rubbing the container main body 2, the heat-treated liquid $S_2$ of a specimen flown into the container main body 2 and the adsorbent $S_3$ are stirred and mixed to obtain a slurry-like suspension $S_4$, and impurities in the heat-treated liquid $S_2$ of the specimen are allowed to be adsorbed to the adsorbent $S_3$ and removed (see FIG. 3C).

Figure 4A:
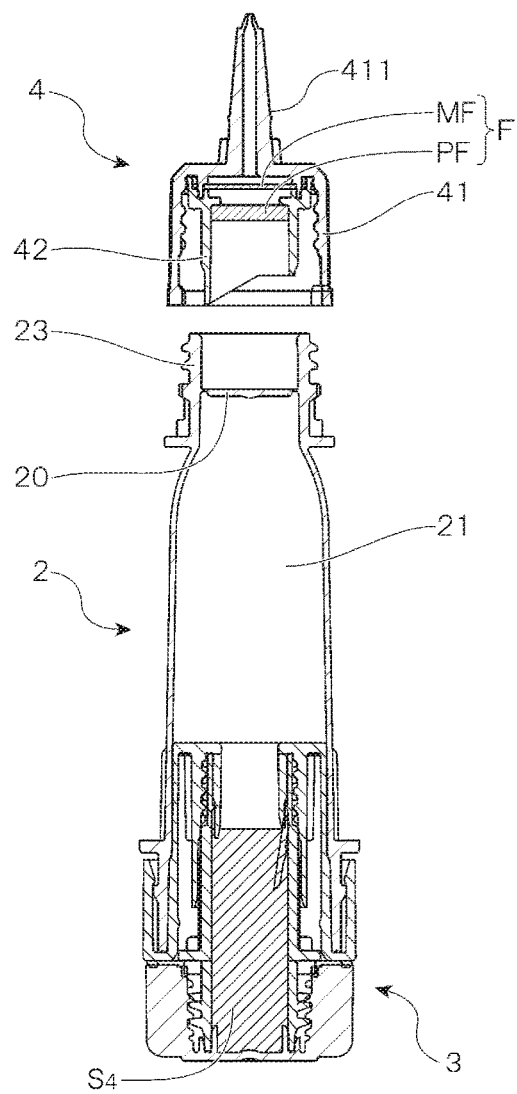
FIGS. 4A and 4B are explanatory views showing a step in which a discharge member with a filter is attached to a contents take-out port of the container main body and the contents take-out port of the container main body is opened.
Figure 4B:
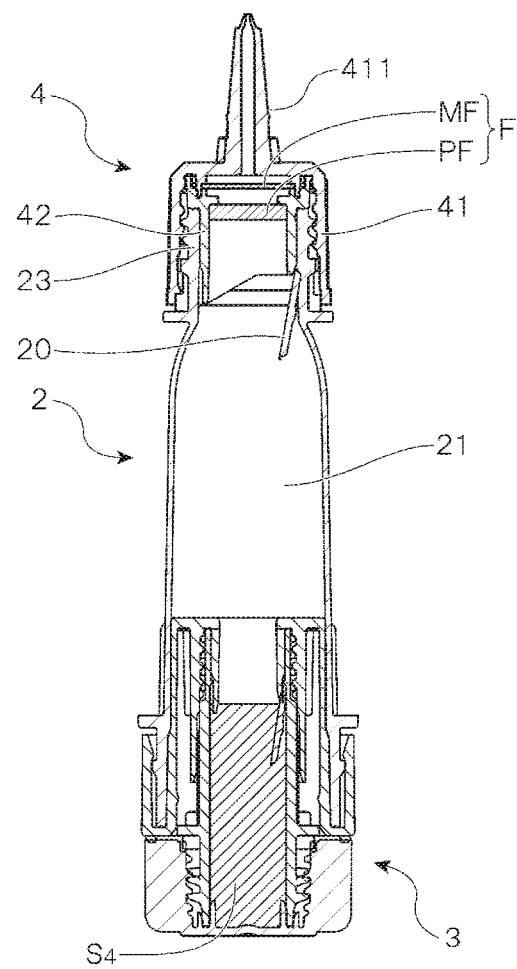

Thereafter, in the state that the contents take-out port 23 of the container main body 2 is directed upward to allow the container main body 2 to be inverted such that the suspension $S_4$ is away from the contents take-out port 23 (see FIG. 4A), the discharge member 4 with a filter is attached to the contents take-out port 23. At this time, by the cutting portion 42 provided in the discharge member 4 with a filter, the partition wall 20 that blocks the contents-takeout port 23 is cut, and the contents take-out port 23 is opened (see FIG. 4B).

Figure 5A:
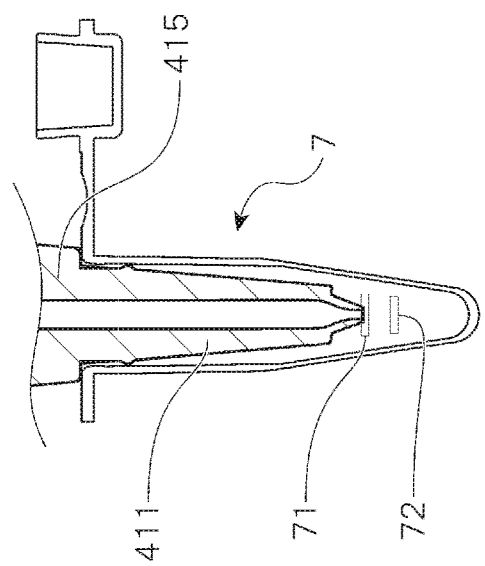
FIGS. 5A to 5C are explanatory views showing a step in which a specimen preparation liquid is dripped into the dripping container.

Subsequently, the container main body 2 is returned to be in an erected state, and the discharge port 411 is inserted into the dripping container 7 (see FIG. 5A).

In the dripping container 7, an upper liquid level line 71 that shows the upper limit of an appropriate amount of the specimen preparation liquid and a lower liquid level line 72 that shows the lower limit of an appropriate amount of the specimen preparation liquid are marked. For example, if the appropriate amount is 25 to 35 µL, the amount of the liquid indicated by the upper liquid level line 71 is 35 µL, and the amount of the liquid indicated by the lower liquid level line 72 is 25 µL.

Then, when the discharge port 411 is inserted into the dripping container 7, by allowing the positioning protrusion portion 415 formed at the base portion of the discharge port 411 to contact the opening edge of the dripping container 7, positioning of the insertion direction is conducted such that the tip of the discharge port 411 is overlapped with the upper liquid level line 71.

Figure 5B:
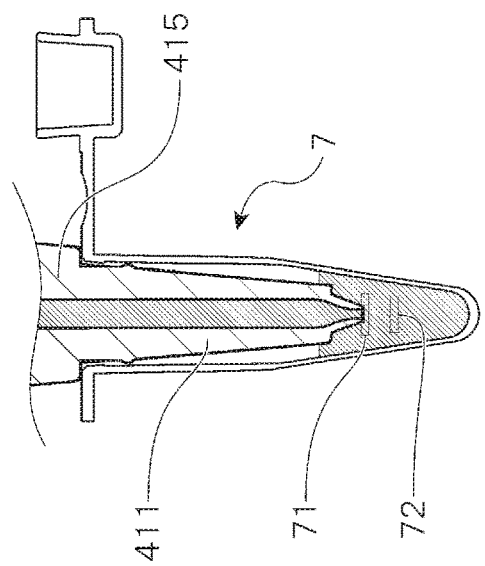
Figure 5C:
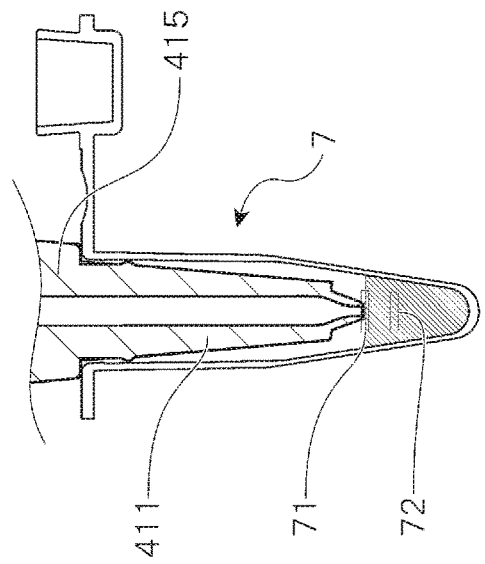

After inserting the discharge port 411 into the dripping container 7, by pressing the container main body 2, while filtering the suspension $S_4$ through a filter F by acting a back pressure on the suspension $S_4$, the filtered specimen preparation liquid $S_5$ is dripped into the dripping container 7. At this time, when the liquid level of the specimen preparation liquid $S_5$ that is injected into the dripping container 7 exceeds the upper liquid level line 71 and a dripped amount becomes excessive (see FIG. 5B), a force pressing the container main body 2 is lessened to allow the container main body 2 to be elastically restored, and an excessive portion is suctioned, whereby the liquid level of the specimen preparation liquid $S_5$ injected into the dripping container is allowed to coincide with the upper liquid level line 71 (see FIG. 5O).

By doing so, the amount of the specimen preparation liquid injected into the dripping container 7 can be always appropriate. However, if fine particles of the adsorbent caught by the filter F when filtering the suspension prevents liquid flow at the time of suction, the suctioning operation takes time, and if a malfunction is significant, a disadvantage occurs that an excessive portion of the specimen preparation liquid dripped into the dripping container 7 cannot be suctioned.

In the present embodiment, the filter F provided in the discharge member 4 with a filter is allowed to be a composite filter in which a pre-filter PF formed of continuous porous foam that is softened at least in a wet state is arranged on the filtration surface side of the membrane filter MF. As a result, when suctioning a specimen preparation liquid that is excessively dripped into the dripping container 7 from the discharge port 411 as mentioned above, the time incurred for the suctioning operation can be shortened, and a fixed amount of a specimen preparation liquid can be dripped into the dripping container with excellent operability without the need of the skill of the operator.

It is thought that these effects are caused by the following reasons:

When the membrane filter MF is used singly, fine particles of the adsorbent caught by the filtration surface block pores of the membrane filter MF, whereby clogging tends to occur easily. When clogging occurs in the membrane filter MF, the liquid flow in a direction reverse to the direction of filtering at the time of suctioning the excessive portion is hindered. However, by providing the pre-filter PF, the amount of fine particles caught by the membrane filter MF can be reduced, thereby allowing clogging of the membrane filter MF to hardly occur. It is thought that, by using the pre-filter PF that is softened at least in a wet state, even if fine particles caught by the pre-filter PF block the pores thereof, the pre-filter PF is elastically deformed by being pushed by the liquid flow when suctioning the excessive portion, the fine particles caught tend to be easily released, and it is possible not to hinder the liquid flow.

Here, taking into consideration easiness in attachment or accuracy of attachment to the discharge member 4 with a filter, the pre-filter PF may have certain rigidity in a dry state and be softened in a wet state by absorbing water in a suspension at the time of operation. The pre-filter PF may be as much softened in a dry state as in a wet state. The "softened at least in a wet state" means both.

In the shown example, the pre-filter PF is arranged on the filtration surface side of the membrane filter MF with a gap. The pre-filter PF may be arranged so as to overlap with the membrane filter MF.

In order to allow the above-mentioned effects to be exhibited without deteriorating dripping performance and filtering performance, the pre-filter PF may have an average pore diameter of 130 to 180 μm and a porosity of 89 to 91% in a wet state as at the time of operation.

If the average pore diameter and the porosity are less than the above-mentioned range, there is a tendency that the filtration flow rate is decreased to deteriorate the dripping performance. If the average pore diameter and the porosity exceed the above-mentioned range, there is a tendency that the amount of fine particles transmitted the pre-filter PF becomes large, and the suctioning performance is deteriorated by clogging of the membrane filter MF.

The pre-filter PF may have a compression stress of 2.9 to 6.3 kPa in a wet state as at the time of operation. If the compression stress is less than the above-mentioned range, the pre-filter PF is too soft, and there is a fear that it drops from the discharge member 4 with a filter. If the compression stress exceeds the above-mentioned range, there is a tendency that the flexibility is inferior, and fine particles caught in the pore become hard to be released, whereby suctioning performance is deteriorated.

The compression stress is a compression stress within a range of compression deformation ratio of 20 to 30%.

Further, the pre-filter PF may have a thickness in a dry state of 1 to 3 mm. If the thickness is less than the above-mentioned range, there is a tendency that the suctioning performance is lowered. If the thickness exceeds the above-mentioned range, there is a tendency that the dripping performance is lowered.

If the pre-filter PF that is softened in a wet state is used, such pre-filter PF may have a water-retention ratio of 850% or more such that it is brought into a sufficiently state for a short period of time.

As the material for the pre-filter PF, one that hardly suffers removal of the material and satisfies the above-mentioned conditions may be used. Among these, due to easiness in shape machining when attaching to the discharge member 4 with a filter, polyvinyl alcohol-made sponge (PVA sponge) may be used.

As the membrane filter MF, various filters such as a hydrophilic polyvinylidene-made membrane filter, a hydrophilic polyethylene terephthalate-made membrane filter, a hydrophilic polyether sulfone-made membrane filter that are characterized by the material thereof are known. The membrane filter MF used in this embodiment may be hydrophilic. Among these, it may be possible to use a hydrophilic polyether sulfone-made membrane filter that has a large filtration flow rate.

EXAMPLES

One or more embodiments of the present invention will be explained in more detail referring to the specific examples.

Example 1

In the composite container 1 shown in FIG. 1, 480 mg of zeolite having an average particle diameter of 5 μm was accommodated within the container main body 2, and 0.94 mL of a treatment liquid (main component: sodium hydroxide solution) was accommodated within the sub container 3.

As the filer F which is provided in the discharge member 4 with a filter, a composite filter in which the following pre-filter PF was arranged on the filtration surface side of the following membrane filter MF was used.

Membrane filter MF: "Millipore Express Plus" (hydrophilic PES-made membrane filter, average pore diameter: 0.45 μm), manufactured by Merck KGaA Pre-filter PF: "Bell Eater E(D)" (PVA sponge, average pore diameter: 130 μm in a wet state, porosity: 90% in a wet state, compression stress: 4.7 kPa in a wet state, water retention ratio: 1100%, thickness: 2 mm), manufactured by Aion Co. Ltd.

Ten sets of such composite container 1 were prepared. In each composite container 1, the sub container 3 was attached to the attachment part 22 of the container main body 2 and the treatment liquid in the sub container 3 was flown into the container main body 2, and the treatment liquid was sufficiently stirred and mixed with the zeolite accommodated within the container main body 2, whereby a slurry-like suspension liquid was prepared. Among these, for five sets, an evaluation test for dripping performance was conducted, and for the remaining five sets, an evaluation test for suctioning performance was conducted.

(Evaluation Test for Dripping Performance)

The discharge member 4 with a filter was attached to the container main body 2, and the contents take-out port 23 thereof was opened. The discharge port 411 was inserted into the dripping container 7 and the filtrate was dripped, and the time taken from the dripping was initiated until the liquid level reached the upper liquid level line 71 (liquid amount: 35 μL) marked on the dripping container was measured. The average value measured for the five sets of the composite container 1 was shown in Table 1.

(Evaluation Test of Suctioning Performance)

The discharge member 4 with a filter was attached, and the contents take-out port 23 of the container main body 2 was opened. The discharge port 411 was inserted into the dripping container 7 and the filtrate was dripped, and the suctioning operation started when the amount of the injected filtrate became 90 μL. The time taken from the suctioning operation was initiated until the liquid level reached the upper liquid level line 71 (liquid amount: 35 μL) marked on the dripping container was measured. The average value measured for the five sets of the composite container 1 was shown in Table 1.

(Evaluation Test of Filtering Performance)

Five dripping containers 7 into which a filtrate was injected in the above-mentioned evaluation tests were arbitrary selected. For each filtrate, the absorbance at a wavelength of 596 nm was measured by using a 5 mm-cell and an evaluation test for filtering performance was conducted. The average values thereof are shown in Table 1.

TABLE 1

|  | Dripping performance (sec.) | Suctioning performance (sec.) | Filtration performance (ABS596 nm) |
|---|---|---|---|
| Example 1 | 9.1 | 3.8 | 0.140 |
| Example 2 | 7.8 | 1.4 |  |
| Example 3 | 14.2 | 1.0 |  |
| Example 4 | 31.3 | 22.2 |  |
| Comp. Ex. 1 | 7.5 | 33.6 | 0.181 |

Example 2

Evaluation tests for dripping performance and suctioning performance were conducted in the same manner as in Example 1, except that, as the pre-filter PF, PVA sponge manufactured by Eagle Kasei Co., Ltd. (average porosity: 130 μm in a wet state, porosity: 90% in a wet state, compression stress: 2.9 kPa in a wet state, water retention ratio: 950%, thickness: 2 mm) was used.

As for each of dripping performance and suctioning performance, eight sets of composite container 1 were prepared respectively and the evaluation tests were conducted. The results are shown in Table 1.

Example 3

Evaluation tests for dripping performance and suctioning performance were conducted in the same manner as in Example 1, except that, as the pre-filter PF, "AC sponge P" manufactured by A.C. Chemical Inc. (PVA sponge, average pore diameter in a wet state: 130 μm, porosity: 90% in a wet state, water retention rate: 1100%, thickness: 2 mm) was used.

As for each of dripping performance and suctioning performance, eight sets of composite container 1 were prepared respectively and the evaluation tests were conducted. The results are shown in Table 1.

Example 4

Evaluation tests of dripping performance and suctioning performance were conducted in the same manner as in Example 1, except that, as the pre-filter PF, "Pyorous EVA" (ethylene-vinyl acetate copolymer sponge, average pore diameter in a wet state: 25 μm, porosity: 77% in a wet state, water retention rate: 340%, thickness: 1 mm) was used.

As for each of dripping performance and suctioning performance, three sets of composite container 1 were prepared respectively and the evaluation tests were conducted. The results are shown in Table 1.

Comparative Example 1

Evaluation tests for dripping performance, suctioning performance and filtering performance were conducted in the same manner as in Example 1, except that the membrane MF was used singly without using the pre-filter PF.

Hereinabove, one or more embodiments of the present invention were explained. The present invention is not limited to the above-mentioned embodiments, and it is needless to say that various modifications are possible within the scope of the present invention.

For example, in the above-mentioned embodiments, an explanation was made on the discharge member 4 with a filter used in the composite container 1 provided with the container main body 2 and the sub container 3, and has a cutting portion 42 that cuts the partition wall 20 that blocks the contents take-out port 23 of the container main body 2 to open the contents take-out port 23. The specific configuration of the discharge member 4 with a filter according to the present invention is not limited thereto.

Further, in the above-mentioned embodiments, an explanation was made taking as an example a case in which one or more embodiments of the present invention are applied to the composite container 1, and a specimen preparation liquid for examining the presence of pathogenic bacteria such as M. tuberculosis in the LAMP method is prepared. The present invention is, however, not limited thereto.

The discharge member with a filter according to one or more embodiments of the present invention can be used widely in various fields as a discharge member with a filter for injecting a fixed amount of a filtrate in the dripping container while filtering a suspension, and if the amount of a dripped filtrate is excessive, the excessive portion can be suctioned, thereby allowing a fixed amount of a filtrate to be injected into the dripping container.

Further, the discharge member with a filter according to one or more embodiments of the present invention may be one in which the filter F that filtrates a suspension is a composite filter in which the pre-filter PF formed of continuous porous foam that is softened at least in a wet state is arranged on the filtration surface side of the membrane filter MF. Features other than these may be appropriately modified without being restricted to the above-mentioned embodiment. The features mentioned in the above-mentioned embodiments may be chosen and combined appropriately.

The documents described in the specification and the Japanese patent applications claiming the priority under the Paris Convention to the invention are incorporated herein by reference in its entirety.

The discharge member with a filter according to one or more embodiments of the present invention can be widely used in various fields as a member for dripping a fixed amount of a filtrate while filtering a suspension.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

EXPLANATION OF NUMERICAL SYMBOLS

4. Discharge member with a filter
7. Dripping container
F. Filter
MF. Membrane filter
PF. Pre-filter

What is claimed is:

1. A container comprising:
a discharge member comprising a filter; and
a container main body containing a suspension,
wherein the suspension contains fine particles of an adsorbent,
wherein the discharge member is configured to be attached to an opening of the container containing the suspension, so that when a pressure in the container is higher than an outside pressure, the suspension is filtered by the filter and a filtrate is dripped into a dripping container via the filter and so that when a pressure in the container is lower than an outside pressure, a fluid flows from the outside of the container to the inside of the container via the filter,
wherein the filter is a composite filter comprising: a pre-filter formed of continuous porous foam that is softened at least in a wet state and that is elastically deformable; and a membrane filter,
wherein the pre-filter is a polyvinyl alcohol (PVA) sponge arranged on a filtration surface side of the membrane filter,
wherein the pre-filter has an average pore diameter of 130 to 180 μm in the wet state, a porosity of 89 to 91% in the wet state, and a compression stress of 2.9 to 6.3 kPa in the wet state, and
wherein a water retention ratio of the pre-filter is 850% or more.

2. The container according to claim 1, wherein the membrane filter is a hydrophilic membrane filter.

3. The container according to claim 1, wherein the adsorbent has an average particle diameter of 5 μm.

4. The container according to claim 1, wherein the adsorbent is selected from the group consisting of alumina, silica, and zeolite.

* * * * *